US011129840B2

(12) United States Patent
Ellis-Grosse

(10) Patent No.: US 11,129,840 B2
(45) Date of Patent: Sep. 28, 2021

(54) METHODS FOR IDENTIFYING NOVEL DOSING REGIMENS

(71) Applicant: Evelyn Ellis-Grosse, San Diego, CA (US)

(72) Inventor: Evelyn Ellis-Grosse, San Diego, CA (US)

(73) Assignee: Zavante Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/476,495

(22) PCT Filed: Jan. 9, 2018

(86) PCT No.: PCT/US2018/013030
§ 371 (c)(1),
(2) Date: Jul. 8, 2019

(87) PCT Pub. No.: WO2018/129560
PCT Pub. Date: Jul. 12, 2018

(65) Prior Publication Data
US 2020/0000830 A1 Jan. 2, 2020

Related U.S. Application Data

(60) Provisional application No. 62/444,346, filed on Jan. 9, 2017.

(51) Int. Cl.
*A61K 31/665* (2006.01)
*A61P 31/04* (2006.01)
(Continued)

(52) U.S. Cl.
CPC .......... *A61K 31/665* (2013.01); *A61K 31/407* (2013.01); *A61K 31/431* (2013.01);
(Continued)

(58) Field of Classification Search
CPC .. A61K 31/665; A61K 31/407; A61K 31/431; A61K 31/546; A61P 31/04
See application file for complete search history.

(56) References Cited

U.S. PATENT DOCUMENTS

2010/0063005 A1 3/2010 Fiala
2015/0132382 A1 5/2015 Dedhiya et al.
2016/0346354 A1 12/2016 Heslet et al.

OTHER PUBLICATIONS

Perry et al., Drugs, 1999;57(5):805-843 (Year: 1999).*

(Continued)

*Primary Examiner* — San Ming R Hui
(74) *Attorney, Agent, or Firm* — Lewis Kohn & Walker LLP; David M. Kohn

(57) ABSTRACT

Methods of treating a Gram negative bacterial infection comprising a co-administration regimen of an effective amount of fosfomycin together with at least one antimicrobial agent selected from the group consisting of piperacillin-tazobactam, ceftazidime and meropenem to an infected subject. A further method of treating a subject with a bacterial infection that includes infection with a "resistant" mutant subpopulation selected from the group consisting of *Staphylococcus aureus, Enterococcus faecalis, Pseudomonas aeruginosa, Acinetobacter baumannii* and *E. coli*, the method comprising (a) obtaining a sample from a subject suffering from a bacterial infection; (b) identifying the presence of the "resistant" mutant subpopulation in said sample; and (c) co-administering fosfomycin and at least one antimicrobial agent to the subject, wherein after the co-administration, the bacterial density is effectively reduced and the "resistant" mutant subpopulation is inhibited.

9 Claims, 2 Drawing Sheets

(51) Int. Cl.
  *A61K 31/407* (2006.01)
  *A61K 31/431* (2006.01)
  *A61K 31/546* (2006.01)
  *G01N 33/569* (2006.01)

(52) U.S. Cl.
  CPC ............ *A61K 31/546* (2013.01); *A61P 31/04* (2018.01); *G01N 33/56916* (2013.01); *G01N 2800/26* (2013.01); *G01N 2800/52* (2013.01)

(56) References Cited

OTHER PUBLICATIONS

Rodriguez et al., Drugs Exptl. Clin. Res., 1980;6(4):281-288 (Year: 1980).*

Pruekprasert et al., "In vitro activity of fosfomycin-gentamicin, fosfomycin-ceftazidime, fosfomycin-imipenem and ceftazidime-gentamicin combinations against ceftazidime-resistant pseudomonas aeruginosa." (Sep. 2005) Southeast Asian J Trop Med Public Health, 36(5).

Okazaki et al., "Effectiveness of fosfomycin combined with other antimicrobial agents against multidrug-resistant Pseudomonas aeruginosa isolates using the efficacy time index assay." (2002) J Infect Chemother 8:37-42, p. 40, Table 3.

Kastoris et al., "Synergy of fosfomycin with other antibiotics for Gram-positive and Gram-negative bacteria." (2010) Eur J Clin Pharmacol 66:359-368, p. 366, Table 3.

* cited by examiner

METHODS FOR IDENTIFYING NOVEL DOSING REGIMENS

CROSS REFERENCE TO RELATED APPLICATIONS

This application is a U.S. national phase application under 35 U.S.C. § 371 claiming priority to International Application No. PCT/US2018/013030 filed Jan. 9, 2018, which claims the benefit of priority from U.S. Provisional Patent Application No. 62/444,346 filed Jan. 9, 2017.

FIELD OF THE INVENTION

The present invention provides a method for identification of new dosing strategies which optimize the probability of positive treatment outcomes in mammals. Specifically, the present invention provides a method of novel dosing regimens for treatment and prevention of the hetero-resistant subpopulation of gram-negative and gram-positive bacteria using fosfomycin, FOS, for injection or oral administration, either alone or in combination with other agents.

BACKGROUND OF THE INVENTION

ZTI-01 (fosfomycin, FOS, for injection) demonstrates broad spectrum activity in vitro including multi-drug resistant (MDR) organisms. FOS shows no cross-resistance to other antibiotic classes and FOS mechanism of action uniquely inhibits an earlier step in peptidoglycan biosynthesis. Other antibiotic agents in combination with FOS have been proposed to enhance bacterial killing of MDR organisms. It is crucial to understand the pharmacokinetics (PK) of antimicrobials to assess the PK/pharmacodynamic parameter associated with efficacy as well as the safety, tolerability, and PK of a single dose of ZTI-01 and oral (PO) fosfomycin tromethamine in healthy subjects.

ZTI-01 is under United States (US) development to treat complicated urinary tract infections in hospitalized patients. The MOA differentiates FOS from other classes of antibiotics. FOS inhibits an early step in cell wall synthesis via covalent binding to MurA. FOS demonstrates broad in vitro activity against Gram-negative (GN) and -positive (GP) bacteria, including multi-drug resistant (MDR) organisms. Differing MOA antibiotic combinations are frequently employed to treat concerning MDRs and optimal FOS combinations producing synergy and lacking antagonism are still necessary.

CLSI interpretive criteria, based on the oral formulation, exist only for urinary tract isolates of *Enterococcus faecalis* (EF) and *Escherichia coli* (EC) for agar dilution (AD; 25 µg/mL glucose-6-phosphate [G6P] supplementation) and disk diffusion (DD) methods. ZTI-01 for cUTI at a dosage of 6 g 8 hr is the sole member of the epoxide antibiotic class. The unique MOA acts at an earlier step in cell wall synthesis inhibition compared to other agents. Therefore, FOS is unaffected by common resistance mechanisms found in Gram-negative (GN) and -positive (GP) bacteria.

Activity with a primarily renal route of elimination makes ZTI-01 a potentially favorable treatment for cUTI patients. Phase 1 data were used to develop a population PK (PPK) model to describe the time-course of fosfomycin and to evaluate potential Phase 2/3 sparse PK sampling strategies.

In light of the above, it is an object of the present invention to provide the desired features described herein as well as additional advantages such as decreasing the potential for on-therapy drug resistance.

SUMMARY OF THE INVENTION

The present invention provides for methods of treating a Gram negative bacterial infection comprising a co-administration regimen of an effective amount of fosfomycin together with at least one antimicrobial agent selected from the group consisting of piperacillin-tazobactam, ceftazidime and meropenem to an infected subject. Optionally, other antimicrobial agents are combined with the co-administration regimen of fosfomycin and the at least one antimicrobial agent selected from the group consisting of piperacillin-tazobactam, ceftazidime and meropenem to an infected subject.

In one aspect, the Gram negative bacterial infection is an infection caused by *Klebsiella pneumoniae*. In another aspect, wherein the Gram negative bacterial infection is an infection caused by *Pseudomonas aeruginosa*. In yet another aspect, the Gram negative bacterial infection is an infection caused by *Acinetobacter baumannii*.

In one aspect, the present invention further provides for a co-administration regimen wherein the effective amount of fosfomycin is greater than the effective amount of the at least one antimicrobial agent when co-administered to the infected subject. Alternatively, the effective amount of fosfomycin is less than the effective amount of the at least one antimicrobial agent when co-administered to the infected subject.

The present invention further provides for a method of treating a subject with a bacterial infection that includes infection with a "resistant" mutant subpopulation selected from the group consisting of *Staphylococcus aureus, Enterococcus faecalis, Pseudomonas aeruginosa, Acinetobacter baumannii* and *E. coli*, the method comprising (a) obtaining a sample from a subject suffering from a bacterial infection; (b) identifying the presence of the "resistant" mutant subpopulation in said sample; and (c) co-administering fosfomycin and at least one antimicrobial agent to the subject, wherein after the co-administration, the bacterial density is effectively reduced and the "resistant" mutant subpopulation is inhibited. Preferably, the at least one antimicrobial agent is selected from the group consisting of piperacillin-tazobactam, cephalosporins, meropenem and penicillin. Optionally, other antimicrobial agents are combined with the co-administration of fosfomycin and the at least one antimicrobial agent selected from the group consisting of piperacillin-tazobactam, cephalosporins, meropenem and penicillin.

In one aspect, the present invention further provides for a co-administration regimen wherein the effective amount of fosfomycin is greater than the effective amount of the at least one antimicrobial agent when co-administered to the infected subject. Alternatively, the effective amount of fosfomycin is less than the effective amount of the at least one antimicrobial agent when co-administered to the infected subject.

BRIEF DESCRIPTION OF THE DRAWINGS

The novel features of the present invention are set forth herein embodied in the form of the claims of the invention. Features and advantages of the present invention may be best understood by reference to the following detailed description of the invention, setting forth illustrative embodiments and preferred features of the invention, as well as the accompanying drawings, of which:

DETAILED DESCRIPTION OF THE INVENTION

Figure 1:
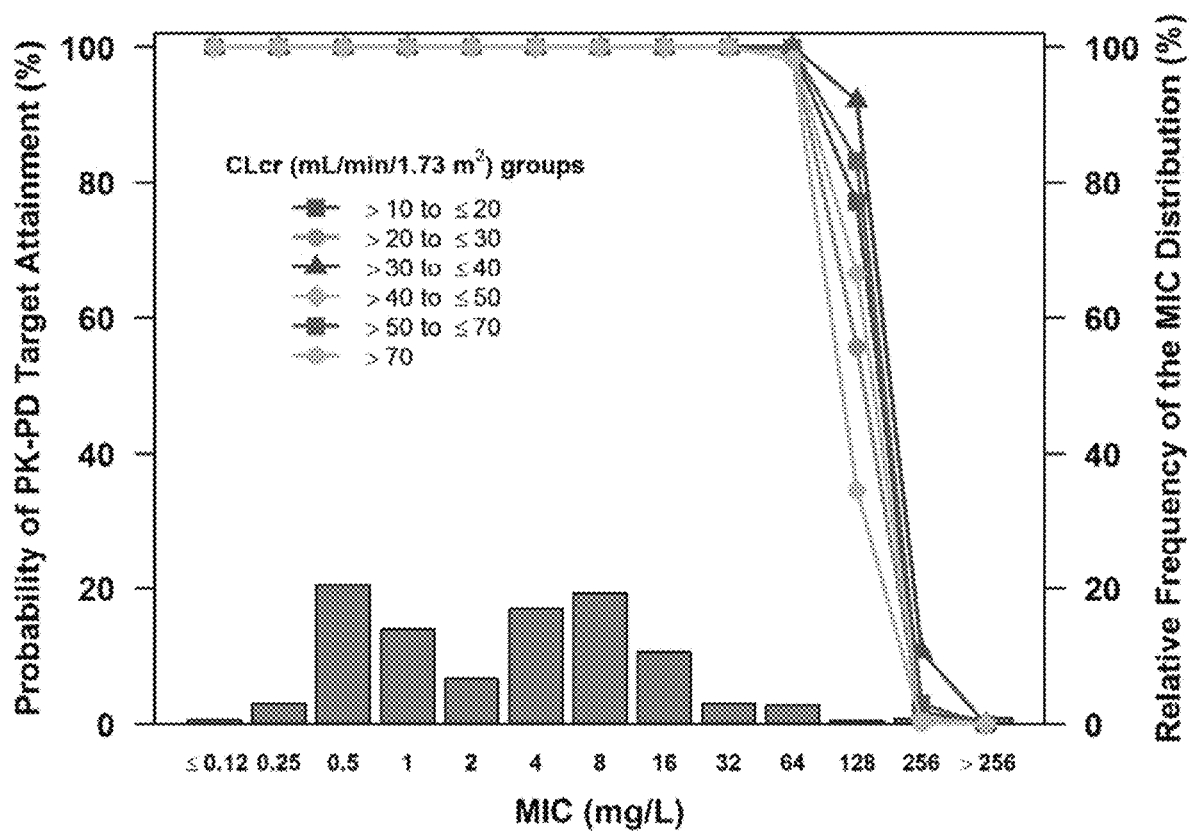
FIG. 1 depicts percent probabilities of PK-PD target attainment by MIC based on the AUC:MIC ratio target associated with net bacterial stasis among stimulated patients by renal function group after administration of ZTI-01 6 g q8 h-based dosing regimens, overlaid on the fosfomycin MIC distribution for Enterobacteriaceae.

The invention can be better visualized by turning now to the following examples.

EXAMPLES

Example 1: Time Kill Analyses of Concerning Gram Negative Bacteria (GNB) by Fosfomycin Alone and in Combination with Select Antimicrobial Agents Methods:

Time-kill kinetic analyses (TKK) were performed on select bacterial strains which demonstrated synergy when tested by checkerboard analysis with FOS and comparator agents. Broth microdilution for FOS (Mueller-Hinton broth supplemented with 25 µg/mL glucose-6-phosphate) and comparators was performed before performing TKK. TKK employed MIC multiples for FOS, and ¼ and 1×MIC of select comparators, and combinations of FOS and comparator. TKK were sampled for colony counts at $T_0$, $T_2$, $T_4$, $T_8$ and $T_{24}$ hours (h). Two Klebsiella pneumoniae isolates (one KPC and one ESBL), two Pseudomonas aeruginosa isolates (non-MDR), and one Acinetobacter baumannii isolate (MDR) were tested.

Results:

FOS was bactericidal when tested against a K. pneumoniae (KPC-producer) isolate. A >3 $\log_{10}$ reduction in bacterial growth (colony forming units, CFU) occurred by 4 h at 2×MIC. By 24 h with FOS (0.5, 1, and 2×MIC), bacterial growth increased approximately 2 $\log_{10}$. Piperacillin-tazobactam (PTZ) at ¼ and 1×MIC showed little inhibitory activity. At 24 h, bacterial growth was similar to growth control. FOS at 0.5, 1, and 2×MIC in combination with PTZ (¼ and 1×MIC) showed synergy with approximately a 3.8-4.2 $\log_{10}$ reduction at 4 h and a 3.4-5.4 $\log_{10}$ reduction at 24 h. FOS (1, 2, 4×MIC) showed a slight decrease (1.4-2.2 $\log_{10}$ CFU) at 4 h and by 24 h, growth was similar to growth control when tested against an ESBL-producing K. pneumoniae isolate. For ceftazidime (CAZ) at ¼ and 1×MIC, there was a slight decrease (0.9-2.1 $\log_{10}$ CFU) by 4-8 h, and at 24 h CFU were similar to growth control. FOS (1, 2, and 4×MIC) in combination with CAZ showed synergy with a 3.8-4.3 $\log_{10}$ reduction by 8 h (1×CAZ MIC) and at least a 5.1 $\log_{10}$ reduction at 24 h (¼ and 1×CAZ MIC). FOS activity was shown to be synergistic at 24 h when tested at 2, 4 and 8×MIC with either ¼ or 1×CAZ MIC (P. aeruginosa #893949) or ¼ or 1×MIC of meropenem (MEM; P. aeruginosa #889839). Against A. baumannii, FOS was shown to be synergistic at 24 h when tested at 0.5, 1 and 2×MIC with MEM (1×MIC).

Conclusions:

Data show that combining two cell wall active agents, FOS plus selected β-lactams, provided enhanced killing and in vitro synergy against concerning GNB.

Example 2: Fosfomycin Activity when Tested Against Gram-Positive and Gram-Negative US Isolates Collected by the SENTRY Antimicrobial Surveillance Program Methods:

FOS was tested against over 1,400 GN and 800 GP clinical isolates collected in US medical centers as part of the SENTRY Antimicrobial Surveillance Program (96% of isolates from 2015) and a selection of 29 GN and 20 GP anaerobes. Isolates were susceptibility (S) tested against FOS and comparators by reference agar dilution (25 µg/mL glucose-6-phosphate supplementation) using existing FDA breakpoints of the oral formulation for comparative assessments.

Results:

FOS was very active against selected Enterobacteriaceae ($MIC_{50/90}$, 4/16 µg/mL). For randomly selected Escherichia coli, 100.0% were S to FOS ($MIC_{50/90}$, 0.5/1 µg/mL), and for Klebsiella pneumoniae the FOS $MIC_{50/90}$ was 4/16 µg/mL (97.0%≤64 µg/mL). The FOS $MIC_{50/90}$ for randomly selected Enterobacter aerogenes, E. cloacae complex, Serratia marcescens, Proteus mirabilis, Citrobacter koseri, and C. freundii complex was 8/16, 8/64, 8/16, 1/8, 1/1, and 0.5/1 µg/mL, respectively. For Pseudomonas aeruginosa and Acinetobacter-baumannii-calcoaceticus complex, higher FOS $MIC_{50/90}$ were observed, 64/128 µg/mL and 128/256 µg/mL, respectively. FOS activity was limited against Prevotella and Porphyromonas spp. (MIC values >256 µg/mL) with variable MICs for the Bacteroides fragilis group (16 to >256 µg/mL; most isolates at >256 µg/mL). MICs against Veillonella spp. ranged from ≤0.03 to 0.06 µg/mL. FOS was very active against Staphylococcus aureus ($MIC_{50/90}$, 4/8 µg/mL) and against coagulase-negative staphylococci (CoNS) excluding S. saprophyticus ($MIC_{50/90}$, 8/64 µg/mL). For S. saprophyticus the FOS $MIC_{50/90}$ were 128/>256 µg/mL. No E. faecalis isolates were resistant to FOS (99.0% S; 1.0% intermediate). E. faecium MICs were generally higher to various antimicrobials including one FOS isolate (19.2% intermediate; 79.8% S). FOS was active against β-haemolytic streptococci (S. pyogenes; $MIC_{50/90}$, 32/64 µg/mL; S. agalactiae; $MIC_{50/90}$, 8/64 µg/mL) and GP anaerobes. MIC values against a small collection of Clostridium spp., Finegoldia magna, and Peptostreptococcus spp. ranged from 0.5 to 32 µg/mL; however, the MICs for Propionibacterium spp. were >256 µg/mL.

Conclusions:

FOS demonstrated broad spectrum activity against a large collection of GN and GP isolates. FOS merits further study in infections where resistant GN and GP bacteria may occur. Potential introduction of an IV form will warrant a reassessment of FDA breakpoints, given the bioavailability limitations of the current oral formulation.

Example 3: Evaluation of the Antimicrobial Activity of Fosfomycin when Combined with Selected Antimicrobial Agents and Tested Against Bacterial Isolates Using Checkerboard Methods Methods:

A total of 40 strains were evaluated: 5 Staphylococcus aureus (SA), 5 Enterococcus faecalis (EF), 5 Pseudomonas aeruginosa (PSA), 5 Acinetobacter baumannii (ACB) and 20 Enterics, including clinical and ATCC strains. Interaction between FOS (with 25 µg/mL glucose-6-phosphate supplement) and up to 10 combination agents was investigated by checkerboard broth microdilution methods against each species/group from a total of 16 antimicrobial agents. Summary fractional inhibitory concentration (ΣFIC) values were calculated for each FOS/agent combination at the minimum, maximum, and mean. ΣFIC was used to classify the combined activity as synergism (SYN; ≤0.5), indifference (INDIF; >0.5 and <4) or antagonism (ANT; ≥4). Indeterminate (INDET) category was assigned when unable to determine combination effects.

Results:

FOS showed no ANT, but showed SYN when combined with multiple agents against isolates from all 5 species/groups (Table 1). Highest rates of SYN were seen when FOS was combined with piperacillin-tazobactam, cephalosporins, meropenem, or penicillin. Other agents showed SYN rates of 10.0% to 40.0% when combined with FOS. Among INDIF isolates, 17.7% had ΣFIC>1 and <4; 16.8% had ΣFIC=1 (additive); 65.5% had ΣFIC>0.5 and <1 (partial synergy).

TABLE 1

Results of Checkerboard Analysis of Fosfomycin Combined with Antimicrobial Agents

| Organism | Combination | No. of strains by interpretive category (% of total) | | | |
|---|---|---|---|---|---|
| (No. tested) | agents | SYN | INDIF | ANT | INDET |
| SA (5) | 10 | 18 (36.0) | 29 (58.0) | 0 (0.0) | 3 (6.0) |
| EF (5) | 7 | 7 (20.0) | 27 (77.1) | 0 (0.0) | 1 (2.9) |
| PSA (5) | 9 | 7 (15.6) | 37 (82.2) | 0 (0.0) | 1 (2.2) |
| ACB (5) | 8 | 13 (32.5) | 21 (52.5) | 0 (0.0) | 6 (15.0) |
| Enteric (20) | 10 | 65 (32.5) | 112 (56.0) | 0 (0.0) | 23 (11.5) |
| All | | 110 (29.7) | 226 (61.1) | 0 (0.0) | 34 (9.2) |

Conclusions:

Nearly 30% of all antimicrobial combinations with FOS were synergistic (ΣFIC≤0.5) and 40% demonstrated partial synergy, which indicates combination therapy with FOS may be beneficial. Importantly, no ANT was observed with any of the FOS combinations.

Example 4: Correlation of Reference Agar Dilution MIC Values and Kirby-Bauer Disk Diffusion Testing for Fosfomycin Against Gram-Positive and Gram-Negative Bacteria Methods:

A total of 938 GN and GP isolates collected in US medical centers were tested against FOS by AD (25 µg/mL [G6P] supplementation) and DD (FOS, 200 µg/50 µg G6P). Interpretive discrepancy rates occurring between disk diffusion results and MIC values were calculated. For analysis purposes, the current CLSI interpretive criteria for EF/EC were applied to all organism groups. No major (ME) or very major (VME) errors occurred when applying interpretive criteria to test results of *Staphylococcus aureus* and coagulase-negative staphylococci. Minor errors (MIE) for coagulase-negative staphylococci were 12.5% in the I+1 to I−1 range; 2.9% MIE overall. For EF, there were no ME/VME and 2.6% MIE (I+1 to I−1); 1.5% MIE overall. ME of 3.9% and 27.5% MIE occurred in the I+1 to I−1 range for *E. faecium*; 3.5 and 24.1% overall. Error rates were high for β-hemolytic streptococci at 23.8% ME and 23.8% MIE overall. The ME rate and MIE rates for Enterobacteriaceae were 10% (1/10) and 30% (3/10) for the I+1 to I−1 range; total error rates were 0.28 and 2.0%, respectively. EC had no ME/VME and only one MIE (0.9%). Error rates were high for *Pseudomonas aeruginosa* (PA) and *Acinetobacter baumannii* (AB).

Conclusions:

The current CLSI MIC and DD interpretive criteria for EC and EF performed well in the correlation of MIC and disk zone diameters. Other enterics and the staphylococci also performed well in the correlation when applying CLSI breakpoints for EC/EF. β-hemolytic streptococci, PA and AB did not perform well. The adequacy of breakpoints to be used for FOS, currently being studied at a dose of 6 g q 8 hr, will need to account for the significantly higher plasma and urine concentrations obtained after IV administration compared to the approved 3 g oral dosage with limited bioavailability. Results from the Phase 2/3 cUTI trial including correlation of MIC and DD testing results will be important in determining the appropriateness of the FDA current breakpoints.

Example 5: Fosfomycin In Vitro Activity Against Bacteria with Various Mechanisms of Resistance to Other Antibacterials from US Hospitals Methods:

Utilizing existing interpretative criteria for the marketed oral agent (dosed at 3 g) for analysis purposes, FOS susceptibility (S) was determined for recent resistant GN and GP clinical isolates including vancomycin-resistant *Enterococcus faecium* (VREM) and *E. faecalis* (VREF); methicillin-resistant *Staphylococcus aureus* (MRSA) and MR coagulase negative staphylococci (MR-CoNS), *Escherichia coli* (EC) and *Klebsiella pneumoniae* (KPN) containing extended spectrum beta-lactamases (ESBL) or were carbapenem resistant (CR); and), *Pseudomonas aeruginosa* (PSA) non-susceptible to ceftazidime (CAZ-NS) or to meropenem (MER-NS). The minimal inhibitory concentration (MIC) of FOS for all isolates was determined by reference agar dilution supplemented with 25 µg/mL glucose-6-phosphate. Isolates were collected from hospitalized patients in the US as a part of the SENTRY surveillance program, 2013-2015.

Results:

The MIC range for 81 VREM was 32 to >256 µg/mL, and 63 isolates had an MIC 64 µg/mL ($MIC_{50/90}$ 64/128 µg/mL). All 101 MRSA had an MIC≤64 µg/mL ($MIC_{50/90}$ 4/8 µg/mL). Of 153 MR-CoNS, 72 had a FOS MIC≤64 µg/mL, 76 *S. saprophyticus* had MICs of 128 to >256 µg/mL, 1 *S. capitis* had an MIC=128 µg/mL, and 1 *S. hominis* had an MIC>256 µg/mL. For 49 EC with an ESBL phenotype, the $MIC_{50/90}$ were 0.5/4 µg/mL; 2 isolates had a FOS MIC>256 µg/mL and the remaining isolates had MIC values ≤32 µg/mL. For 11 EC that were CR, 2 had a FOS MIC>256 µg/mL while 9 had an MIC range of 0.5-32 µg/mL. Of 50 KPN with ESBL phenotype, 49 had a FOS MIC≤64 µg/mL, one isolate MIC was >256 µg/mL, and the $MIC_{50/90}$ were 4/16 µg/mL. For 17 CR-KPN, 16 had a FOS MIC≤64 µg/mL, one isolate had an MIC>256, and the $MIC_{50/90}$ were 8/64 µg/mL. For 38 CAZ-NS PSA, 32 had a FOS MIC≤64 µg/mL, one isolate had an MIC>256 µg/mL, and the $MIC_{50/90}$ were 64/128 µg/mL. For 42 MER-NS PSA, 34 had a FOS MIC≤64 µg/mL, one isolate had an MIC of >256 µg/mL, and the MIC$_{50/90}$ were 64/128 µg/mL.

Conclusion

FOS demonstrated potent activity against recent drug-resistant GN and GP isolates and was unaffected by resistance to other drug classes. Given the bioavailability limitations of the current oral formulation, a reassessment of breakpoints will be warranted by FDA for the IV formulation. These in vitro results indicate that this drug may be useful therapy for infections caused by drug resistant pathogens.

Example 6: Pharmacokinetics, Safety, and Tolerability of Single Dose ZTI-01 (Fosfomycin for Injection) and Oral Fosfomycin in Healthy Volunteers Materials/methods: Phase I, open-label study evaluating IV (ZTI-01) and PO (Monurol®) FOS in healthy adult subjects. Subjects received a single dose of 1 g IV, 8 g IV, and 3 g PO FOS in a randomized, crossover fashion with a washout period in between. Blood and urine samples were collected serially before and through 48 hours post-dose and analyzed via LC/MS-MS. Noncompartmental analyses were performed via WinNonlin. Safety was monitored throughout the course of the study.

Results:

Subject demographics: 39% male, 75% white, mean (±SD) age 26±5 years, mean (±SD) weight 69.9±11.2 kg, mean (±SD) CrCl 139.3±23.9 mL/min. Mean (±SD) plasma PK parameters after IV and PO administration are shown in Table 2. The % relative bioavailability of PO FOS in relation to the 1 g IV dose was 52.8%. The fraction of the dose excreted in urine after 48 hours for 1 g, 8 g IV, and 3 g PO were: 74%, 80%, and 37%, respectively. 80% of subjects reported a treatment-emergent adverse event (TEAE), the majority (67.9%) of which occurred after the 8 g IV dose. All TEAEs were mild-moderate and resolved without sequelae. The most common TEAE after 8 g IV was bradycardia (28.6%), and hypocalcemia (17.9%) after 1 g IV. Headache was the most common (10.7%) FOS-related TEAE. Events were comparable between the groups and no new safety concerns were identified.

TABLE 2

Pharmacokinetics of IV and PO Administration of Fosfomycin

| | FOS regimen | | |
| --- | --- | --- | --- |
| PK parameters | 1 g IV (n = 28) | 8 g IV (n = 28) | 3 g PO (n = 27) |
| $C_{max}$ (mg/L) | 44.3 ± 7.6 | 370 ± 61.9 | 26.8 ± 6.4 |
| $T_{max}$ (h) | 1.1 ± 0.05 | 1.08 ± 0.01 | 2.25 ± 0.4 |
| $V_d$ or $V_d/F^*$ (L) | 29.7 ± 5.7 | 31.5 ± 10.4 | 204 ± 70.7* |
| $CL_T$ or $CL_T/F^*$ (L/h) | 8.7 ± 1.7 | 7.8 ± 1.4 | 17.0 ± 4.7* |
| $CL_R$ (L/h) | 6.6 ± 1.9 | 6.3 ± 1.6 | 6.5 ± 1.8 |
| $AUC_{0-\infty}$ (mg · h/L) | 120 ± 28.5 | 1060 ± 192 | 191 ± 57.6 |
| $t_{1/2}$ (h) | 2.4 ± 0.4 | 2.8 ± 0.6 | 9.04 ± 4.5 |

Conclusion

The plasma PK of ZTI-01 were approximately linear and proportional between the 1 g and 8 g doses. The administration of 3 g of PO FOS resulted in a 1.5-fold higher plasma exposure in terms of $AUC_{0-\infty}$ compared to the 1 g IV dose, but a much lower (5.5-fold) $AUC_{0-inf}$ than that of the 8 g dose. The plasma elimination half-life of PO FOS was longer than that after IV administration, potentially due to "flip-flop kinetics"; i.e. slow absorption into the central compartment. The higher PK exposure and comparable safety profile of ZTI-01 support further investigation in the target patient population. ZTI-01 is under US development to treat complicated cUTI at a daily dosage of 6 g q 8 hrs.

Example 7: Population Pharmacokinetic (PK) Analysis of ZTI-01 (Fosfomycin for Injection) Using Phase 1 Data for ZTI-01 and Evaluation of a Phase 2/3 Sparse PK Sampling Strategy Methods:

The PPK model was developed in NONMEN 7.1.2 using Phase 1 plasma and urine PK data from 28 healthy subjects who received ZTI-01 as single (1 and 8 g infused over 1 hour) IV doses in a crossover fashion. PPK parameters were allometrically scaled to body weight a priori. Published data describing the relationship between fosfomycin PK and creatinine clearance (CLcr) [Fillastre J P et al. Pathologie Biologie 1988; 36: 728-30] were considered. An optimal sampling scheme (OSS) was derived based on the final PPK model and optimal sampling theory (OST) in ADAPT 5. The OSS was evaluated using Monte Carlo simulation. Plasma concentration-time data based on the OSS were generated for simulated patients who received ZTI-01 dosing regimens assigned by CLcr group. Maximum a-posteriori Bayesian estimation based on the OSS was performed in NONMEM to estimate individual PK parameters. Bias, the prediction error percent (PE %) for the Bayesian PK estimates relative to the true values for clearance and steady-state volume of distribution, and precision, the root mean squared error (RMSE) of the true and estimated PK parameters, were calculated.

Results:

A 3-compartment model with zero-order input and first-order elimination best described fosfomycin plasma and urine PK. A sigmoidal equation best described the relationship between renal clearance and CLcr. The PPK model provided an acceptable fit to the plasma data ($r^2$=0.99) while showing acceptable precision when fitting to the urine data ($r^2$=0.87). Based on the PPK model and OST, the optimal times to obtain PK samples identified were 1, 2, 4, and 8 hours after the start of the infusion. All PK parameters were estimated with minimal bias and relatively high precision as evidenced by median PE % values <15% and RMSE estimates <10 across all CLcr groups, respectively.

Conclusions

A PPK model describing fosfomycin PK after administration of ZTI-01 was successfully developed. This model was used to identify an OSS for an ongoing Phase 2/3 study evaluating ZTI-01 for the treatment of hospitalized patients with cUTI.

Example 8: ZTI-01 (FOS, Fosfomycin for Injection) Efficacy Against *Escherichia coli* (EC), *Klebsiella pneumoniae* (KPN) and *Pseudomonas aeruginosa* (PSA) Including Those with Extended Spectrum Beta-Lactamases (ESBL) and Carbapenem Resistant (CR) Phenotypes Methods:

5 EC (4 ESBL), 3 KPN (2 CR), and 2 PSA were used. MICs were determined by agar dilution. Single dose plasma PK was determined in mice after SC administration of 3.125, 12.5, 50, 200, 400 and 800 mg/kg. PK/PD index determination was performed using a dose fractionation (DF) study design. ZTI-01 efficacy was then examined against all 10 isolates (dose range 12.5-6400 mg/kg/24 h). Organism burden after 24 h was enumerated from each thigh infection. The dose-response data was analyzed using the Emax Hill equation. The PK/PD index AUC/MIC associated with net stasis and 1-log kill was determined for all isolates. A dose-ranging survival study using a single isolate was also used to validate the significance PD targets identified.

Results:

MICs ranged from 1-16 mg/L. Single dose PK parameter ranges include: Cmax 0.6-42.4 mg/L, $AUC_{0-\infty}$ 1.4-87 mg*h/L, $T_{1/2}$ 0.51-1.1 h. PK/PD indices regression analysis from the DF study demonstrated: AUC/MIC $R^2$ 0.70, Cmax/MIC $R^2$ 0.51, T>MIC $R^2$ 0.44. Dose-dependent cidal activity was demonstrated against every isolate. Maximal cidal activity was 2-3 log kill and was commonly noted in isolates with the lower fosfomycin MICs. The mean static doses and associated AUC/MIC and T>MIC targets are shown at Table 3, as well as non-linear regression analysis of each PD indice.

TABLE 3

Pharmacokinetic and Statistical Analysis of Fosfomycin against Drug-Resistant Isolates

|     | Static Dose (mg/kg/24 h) | Stasis AUC/MIC | Stasis T > MIC (%) | AUC/MIC Regression ($R^2$) | T > MIC Regression ($R^2$) |
| --- | --- | --- | --- | --- | --- |
| EC  | 847  | 19.3* | 37.7* | 0.72 | 0.55 |
| KPN | 1667 | 11.1* | 26.5* | 0.76 | 0.64 |
| PSA | 1920 | 15    | 29    | 0.92 | 0.87 |

*median targets

Conclusions

ZTI-01 demonstrated in vitro and in vivo potency against EC, KPN and PSA including those with ESBL- and CR- phenotypes. PD index AUC/MIC was most closely linked with efficacy based on R2. PD target AUC/MIC and T>MIC targets were similar between each organism group. Maximal survival was noted at exposures similar to stasis endpoints. These data should prove useful for dosing regimen design and optimization for clinical study. ZTI is currently in US development for cUTI.

Example 9: ZTI-01 (FOS, Fosfomycin for Injection) Activity Against Carbapenem-Resistant and Ceftazidime-Avibactam Resistant Enterobacteriaceae (CRE) Clinical Isolates with Diverse Resistance Mechanisms Methods:

FOS susceptibility was tested using agar dilution in Mueller-Hinton supplemented with 25 µg/mL glucose-6-phosphate. Existing breakpoints for oral FOS were used for comparison: MIC>64 µg/mL defined FOS-R. WGS was performed using Illumina MiSeq.

Results:

50 isolates were tested: 42 Kp (34 KPC, 3 NDM-1, 4 class C-carbapenemase (2 OXA-46, 1 each OXA-181 and OXA-232), and 1 with ESBL and ompK36 mutation), 5 *Enterobacter* spp (all KPC, 1 also NDM-1), 2 *E. coli* (1 NDM-1 and 1 NDM-6), and 1 *K. oxytoca* (KPC-2 and VIM-1). 14 isolates were C-A R: 5 NDM-1, 1 NDM-6, 1 VIM-1, 2 wild-type KPC-3, 5 mutant KPC-3 (D179Y amino acid substitution (n=2), D179Y/T243M (n=2) and V240G (or KPC-8, n=1)). 72% (36) and 40% (20) had mutations within ompK35 and ompK36, respectively. FOS $MIC_{50}$ and $MIC_{90}$ were 2 and 512 µg/mL, respectively. 94% (47) of isolates were susceptible to FOS, including all isolates that were C-A R. Median FOS MIC against C-A R isolates was 8 µg/mL (range: 1-64). Three isolates harbored genes encoding FOS-modifying enzyme fosA2, 1 of which was FOS R (MIC 256 µg/mL). The R isolate also had a SNP in FOS transporter gene glpT. The second FOS-R isolate harbored fosA3 (MIC>1024 µg/mL). The third FOS-R isolate (OXA-181+, CTXM-15+Kp; MIC 128 µg/mL) had unclear mechanisms of R. SNPs were found within glpT (3 isolates, including 1 mentioned above), FOS transporter gene uhpT (3 isolates), and regulator genes ptsI (1 isolate, which also had uhpT) and uhpA (1 isolate). None of these isolates was FOS R. All isolates had wild-type genes encoding FOS target MurA and regulator CyrA. No isolates harbored fosC or fomA/B kinase genes.

Conclusions

FOS is currently in US development for treatment of cUTI and as an IV formulation warrants a reassessment of breakpoints. Utilizing existing oral breakpoints, FOS is highly active against CRE in vitro, including isolates that are C-A R, isolates that harbor class B- and C-carbapenemases, and KPC-Kp with ompK36 porin mutations. Therefore, FOS is active against CRE isolates for which there are currently no β-lactam treatment options.

Example 10: Pharmacokinetics-Pharmacodynamics (PK-PD) Target Attainment Analyses to Support ZTI-01 Dose Selection for Patients with Complicated Urinary Tract Infections (cUTI)

Methods:

Using parameter estimates from a population PK model (3-compartment model with zero-order input and first-order elimination), total-drug plasma concentration-time profiles were generated for 6,000 simulated patients with varying creatinine clearance (CLcr, mL/min/1.73 m$^2$). Simulated patients received ZTI-01 according to CLcr: 6 g IV q8 h for >50 mL/min/1.73 m$^2$, 4 g IV q8 h for >40 to 50 mL/min/1.73 m$^2$, 6 g IV loading followed 3 g IV q8 h for >30 to 40 mL/min/1.73 m$^2$, and 6 g IV load followed by 5 g IV q24 h for >10 to 30 mL/min/1.73 m$^2$. Day 1 $AUC_{0-24}$ was calculated. Percent probabilities of PK-PD target attainment by MIC and overall (i.e., weighted over the MIC distribution for 1,091 Enterobacteriaceae isolates from USA) were determined using median total-drug plasma AUC:MIC ratio targets associated with net bacterial stasis and a 1-$log_{10}$ CFU reductions from baseline at 24 h from a neutropenic murine-thigh infection model for Enterobacteriaceae (19.1 and 41.6, respectively).

Results:

Percent probabilities of attaining total-drug plasma AUC: MIC ratio targets associated with a net bacterial stasis (FIG. 1) and 1 $\log_{10}$ CFU from baseline were ≥98.3% at a MIC of 64 mg/L and ≥97.3% at a MIC of 32 mg/L, respectively, across renal function groups. These MIC values were 1 to 2 dilutions higher than the $MIC_{90}$ of 16 mgL for Enterobacteriaceae. Overall percent probabilities of PK-PD target attainment for both AUC:MIC ratio targets were 97.8 and 95.5%, respectively.

Conclusions

These data provide support for ZTI-01 6 g IV q8 h (and renally-adjusted dosing regimens) for the treatment of patients with cUTI.

Example 11: Activity of Fosfomycin Against Gram-Negative Baseline Bacterial Isolates from Patients in a Phase 3 Complicated Urinary Tract Infection Trial (ZEUS)

Background

ZTI-01 (fosfomycin, FOS, for injection) is under US development to treat complicated urinary tract infections (cUTI). FOS is unique compared to other antimicrobials in that it inhibits an early step in cell wall synthesis via covalent binding to MurA. FOS demonstrates broad in vitro activity against gram-negative (GN) and -positive (GP) bacteria, including organisms containing extended-spectrum β-lactamases (ESBL). In this study, we investigated the activity of FOS against gram-negative clinical isolates from the phase 3 cUTI trial (ZEUS).

Methods:

FOS was tested against 465 GN baseline clinical isolates collected in the cUTI clinical trial. Isolates were susceptibility (S) tested against comparator agents by reference broth microdilution and FOS by reference agar dilution (25 μg/mL glucose-6-phosphate supplementation). Existing FDA FOS breakpoints of ≤64 mg/L for the oral formulation were used for comparative assessments. Screen-positive ESBL Enterobacteriaceae isolates were characterized by whole genome sequencing and analysis for the presence of known β-lactamase genes.

Results:

FOS was very active against Enterobacteriaceae ($MIC_{50/90}$, 1/16 mg/L; 96.4%≤64 mg/L). For 329 *E. coli*, 100.0% were S to FOS ($MIC_{50/90}$, 1/1 mg/L), and for 62 *Klebsiella pneumoniae* the FOS $MIC_{50/90}$ values were 16/128 mg/L (87.1%<64 mg/L). The FOS $MIC_{50/90}$ values for 14 *Enterobacter cloacae* complex and 20 *Proteus mirabilis* were 16/128 and 2/32 mg/L, respectively. For 21 *Pseudomonas aeruginosa*, higher FOS $MIC_{50/90}$ were observed, 64/256 mg/L. Regarding the characterized ESBL-containing isolates, the FOS $MIC_{50/90}$ for 49 *E. coli* were 1/2 mg/L, for 28 *K. pneumoniae* were 16/128 mg/L, and for 3 *P. mirabilis* the $MIC_{50}$ was 2 mg/L. The most common ESBL was CTX-M (42/49 *E. coli* and 27/28 *K. pneumoniae*), with CTX-M-15 (belonging to Group 1) the most common variant. Carbapenemase genes, NDM-1 and OXA-48, were detected in 2 *K. pneumoniae* isolates, which had FOS MICs of 8 and 64 mg/L, respectively.

Conclusion

FOS demonstrated broad-spectrum activity against baseline clinical isolates in a phase 3 cUTI trial, including those with ESBL or carbapenemases. FOS merits further study in infections where resistant GN may occur. Potentially introducing an IV form would warrant a reassessment of susceptibility breakpoints given the current oral formulation's bioavailability limitations.

Example 12: In Vitro Synergy of Fosfomycin (FOF) and Parenteral Antimicrobials Against Carbapenem-Nonsusceptible *Pseudomonas aeruginosa* (PSA)

Background

Infection caused by drug-resistant PSA creates therapeutic dilemmas, especially if the carbapenem-nonsusceptible (NS) phenotype is present. Thus, clinical guidelines are increasingly recommending the use of combination therapy against PSA possessing this profile. Intravenous FOF is undergoing clinical development in the US and as a result of its broad spectrum of activity; inclusion in combination regimens for MDR pathogens appears likely. Herein, we assessed the synergistic potential of FOF against a population of carbapenem-NS PSA possessing diverse phenotypic profiles.

Methods:

Meropenem-NS PSA obtained from US hospitals were studied. MICs of all antibiotics except FOF were previously determined by broth microdilution; FOF MIC was determined by ETEST® antibiotic gradient diffusion strip prior to conducting synergy assessments between FOF and aztreonam (ATM), cefepime (FEP), ceftazidime (CAZ), meropenem (MEM), piperacillin/tazobactam (TZP), and tobramycin (TOB). The synergy potential for each combination was determined by crossing a FOF ETEST® strip with each of the aforementioned antibiotic strips at a 90° angle at their respective MIC with subsequent calculation of the fractional inhibitory concentration. Of note, Liofilchem® MIC Test Strip was used for TZP due to commercial availability. Only organisms that were NS to the 2nd drug were assessed for synergy.

Results:

Among 87 clinical MDR PSA isolates, FOF $MIC_{50/90}$ was 64/>1024 μg/mL. Synergy was detected in 57 of 246 (23.2%) FOF-drug combinations among 39/87 (44.8%) isolates; additivity was demonstrated for 112 (45.5%) combinations among 66 (75.9%) isolates. Importantly, no antagonism was observed. By drug, CAZ most often displayed synergy (16/25, 64.0%), followed by TOB (5/18, 27.8%), and FEP (7/27, 25.9%). FOF-ATM most frequently resulted in additivity as observed for 32 of 47 (68.1%) isolates. TZP produced the fewest synergistic or additive combinations as observed for only 10 of 42 (23.8%) isolates. All other combinations were synergistic or additive for >50% of isolates tested. In combination with FOF, MEM MICs were reduced from ≥8 mg/L to ≤2 mg/L for 12 of 87 isolates (13.8%).

Conclusion

Using an ETEST® method, synergy or additivity was commonly observed between FOF and other antibiotics against MDR PSA. Furthermore, FOF demonstrated ability to restore the activity of meropenem, though this observation warrants further study. These data will aid clinicians in selection of optimal FOF-drug combinations for the treatment infections caused by MDR PSA.

Example 13: In Vitro Investigation of Synergy Among Fosfomycin (FOF) and Various Antimicrobials Against Carbapenemase-Producing Enterobacteriaceae (CPE)

Background

CPE infections pose a serious threat to public health. With the rise of CPE, β-lactams are often rendered ineffective as monotherapy against these recalcitrant pathogens. FOF is a broad-spectrum phosphonic acid derivative currently under development as an intravenous (IV) formulation for use in the U.S. As combination therapy is predominantly employed against CPE, an assessment of synergistic effect of FOF with other antibiotics is warranted to optimize the potential role of IV FOF.

Methods:

Isolates (n=37) harboring KPC, NDM, OXA, or VIM carbapenemases, with a majority also producing extended-spectrum β-lactamases, were acquired from the FDA-CDC Antimicrobial Resistant Bank. MICs for agents tested in combination with FOF were determined by broth microdilution; FOF MIC was determined by ETEST® antibiotic gradient diffusion strip prior to conducting synergy assessments between FOF and aztreonam (ATM), ceftazidime (CAZ), ceftazidime/avibactam (CZA), cefepime, ceftolozane/tazobactam (C/T), meropenem, piperacillin/tazobactam, and tobramycin (TOB). Synergistic potential for each combination was determined by crossing a FOF ETEST® strip with each of the aforementioned antibiotic strips at a 90° angle at their respective MICs with subsequent calculation of the fractional inhibitory concentration (FIC). Notably, Etest has been observed to overcall the FOS MIC by ~2 dilutions higher, however this method provides a conservative and reasonable means to evaluate potential FOS synergy. Only organisms that were non-susceptible to the second drug were assessed for synergy.

Results:

Among 37 CPE tested, including 11 isolates harboring fos(A), FOF $MIC_{50}$ by ETEST® was >1024 µg/mL. Synergy was detected for 16 of 281 (5.7%) FOF-drug combinations tested among 10 of 37 (28.2%) isolates. Additivity was observed for 49 of 281 (17.4%) combinations, while indifference comprised the majority of combinations (76.9%); importantly, no antagonism was observed. By drug, C/T most frequently displayed synergy for 5 of 37 (13.5%) isolates, followed by ATM for 4 of 36 (11.1%) isolates, and CAZ for 3 of 37 (8.1%) isolates. FOF-ATM most frequently resulted in additivity as observed for 11 of 36 (30.6%) isolates. CZA and TOB did not produce any synergistic combinations when tested against CZA-nonsusceptible (n=25) and TOB-nonsusceptible (n=35) isolates.

Conclusion

Using an ETEST® method, synergy and additivity between FOF and commonly utilized broad-spectrum antibiotics was observed for approximately a quarter of all combinations tested. The data support further study of FOF-C/T, FOF-ATM, and FOF-CAZ as these combinations most frequently displayed synergy and/or additivity compared with other combinations studied.

Example 14: Fosfomycin (FOS) Activity Against Carbapenem-Resistant Enterobacteriaceae (CRE) Clinical Isolates with Diverse Resistance Mechanisms Background FOS is a cell wall synthesis inhibitor with bactericidal activity against Enterobacteriaceae. We evaluated in vitro activity of FOS against clinical CRE isolates that had diverse resistance mechanisms.

Methods:

FOS susceptibility was tested using agar dilution in Mueller-Hinton supplemented with 25 µg/mL glucose-6-phosphate. Synergy was assessed by disc diffusion, at between-disc distances of 15 and 20 mm. Breakpoints for oral FOS were used (MIC>64 µg/mL defined FOS-R).

Results:

50 isolates were tested: 41 *K. pneumoniae* (Kp), 5 *Enterobacter cloacae*, 2 *E. coli*, 1 *K. oxytoca*, and 1 *E. aerogenes*. Resistance mechanisms included KPC (39), NDM (7), class C-OXA (4), and AmpC (7). Non-susceptiblity rates were: Meropenem (MEM) 82%, Imipenem (IMP) 86%, Pipercillin-tazobactam (P-T) 96%, Ciprofloxacin (CIP) 84%, Gentamicin (GEN) 54%, Ceftazidime (CAZ) 92%, CAZ-avibactam (C-A) 6%, Ceftolozane-tazobactam (C-T) 43%. 3 isolates exhibited FOS MIC>64 µg/mL, each of which was also not susceptible to MEM, IMP, P-T, GEN and C-T. Synergy was observed at 15 mm distances, but not 20 mm. Synergy rates between FOS and other agents against FOS-S isolates were: MEM 19%, IMP 23%, P-T 6%, CIP 8%, GEN 11%, CAZ 4%, C-A 53%, C-T 11%. Synergy rates based on S of the second agent were: MEM-S 56% vs. MEM-R 10% (p=0.0008), IMP-S 86% vs IMP-R 12% (p=0.0003), P-T-S 50% vs. P-T-R 4% (p=0.12), CIP-S 57% vs CIP-R 0% (p=0.0002), GEN-S 22% vs. GEN-R 0% (p=0.02), CAZ-S 0% vs CAZ-R 5%, C-A-S 53% vs. C-A-R 53%, C-T-S 57% vs C-T-R 2% (p=0.009). For FOS-R isolates, synergy was only seen with C-A (n=1). 3 isolates harbored genes encoding FOS-modifying enzyme fosA2, 1 of which was FOS R (MIC 256 µg/mL). The R isolate also had a SNP in FOS transporter gene glpT. The second FOS-R isolate harbored fosA3 (MIC>1024 µg/mL). The third FOS-R isolate (OXA-181+, CTXM-15+Kp; MIC 128 µg/mL) had unclear mechanisms of R. SNPs were found within glpT (3 isolates, including 1 mentioned above), FOS transporter gene uhpT (3 isolates), and regulator genes ptsI (1 isolate, which also had uhpT) and uhpA (1 isolate). None of these isolates was FOS R. All isolates had wild-type genes encoding FOS target MurA and regulator CyrA. No isolates had fosC or fomA/B kinase genes.

Conclusions

FOS was highly active against CRE in vitro, including isolates that were R to broad-spectrum antibiotics including new agents C-A and C-T. Therefore, FOS was active against CRE isolates for which there are currently no active β-lactams. In general, synergy rates between FOS and other agents were excellent when both agents were active. Synergy rates between FOS and C-A were high, even if isolates were C-A R. Therefore, FOS holds great promise as a combination agent against CRE infections. Synergy was only observed at 15 mm between-disc distances, which indicates that optimizing pharmacokinetics will be crucial to positive interactions between agents in vivo.

Example 15: Evaluation of In Vitro Activity of Fosfomycin Alone and in Combination with Other Agents Against Carbapenem Resistant *Pseudomonas aeruginosa* Clinical Isolates

Background

Carbapenem resistant *Pseudomonas aeruginosa* (CR-Pa) have emerged as major pathogens worldwide. Antibiotic treatment response rates among patients with CR- and other highly-resistant Pa infections are poor, even for newly-developed agents like the β-lactam/β-lactamase inhibitors ceftolozane-tazobactam (CFT-TAZ) and ceftazidime-avibactam (CAZ-AVI). Fosfomycin (FOS) inhibits UDP-N-acetylglucosamine enolpyruvyl transferase (MurA), an enzyme that catalyzes the first step in bacterial cell wall synthesis. FOS has broad-spectrum activity against aerobic Gram-negative and Gram-positive bacteria. Due to its unique mechanism of action, FOS has particular promise in combination regimens against Pa, offering a prospect of synergy with other antibiotics. Our objective was to study the in vitro activity of FOS against well-characterized Pa clinical isolates, alone and in combination with other agents.

Methods:

Forty-three Pa isolates (recovered from unique patients) were selected for testing. Single drug minimum inhibitory concentrations (MICs) were determined for FOS, CAZ-AVI, CFT-TAZ, gentamicin (GEN), ciprofloxacin (CIP), meropenem (MER), imipenem (IMP), pipercillin-tazobactam (PIP-TAZ), and CAZ by agar dilution (Mueller-Hinton agar with 25 ug/mL glucose-6-phosphate (G6P) at 35° C. (CLSI method)). Interactions between FOS and other agents were determined by double disc testing on Mueller Hinton agar. Discs containing 300 μg FOS and 50 G6P were used, along with commercially available Kirby Bauer discs for other agents. Intravenous FOS MIC breakpoints are not established. We defined MIC≤64 ug/mL and >64 ug/mL as susceptible (S) and non-susceptible (NS), respectively (i.e., breakpoints for oral FOS vs. Enterobacteriaceae). Time kill assays against 12 isolates were performed for FOS, CAZ-AVI, CFT-TAZ and PIP-TAZ (alone, and each agent in combination with FOS) at the respective MIC (or breakpoint MIC for resistant isolates). Bactericidal activity during time-kills was defined as >3-$\log_{10}$ reduction at 12 and/or 24 hours, compared to starting inoculum. Synergy during time-kills was defined as >2-$\log_{10}$ reduction at 12 and/or 24 hours, compared to best single agent alone.

Results:

S and NS rates for each agent, based on MICs, are shown in Table 4.

TABLE 4

S and NS Rates for Various Drugs against Pa Isolates

| Drug | S % (n) | NS % (n) |
|---|---|---|
| FOS | 70% (30) | 30% (13) |
| CAZ-AVI | 74% (32) | 26% (11) |
| CFT-TAZ | 88% (38) | 12% (5) |
| GEN | 70% (30) | 30% (13) |
| CIP | 60% (26) | 40% (17) |
| MER | 40% (17) | 60% (26) |
| IMP | 42% (18) | 58% (25) |
| PIP-TAZ | 51% (22) | 49% (21) |
| CAZ | 58% (25) | 42% (18) |

Figure 2:
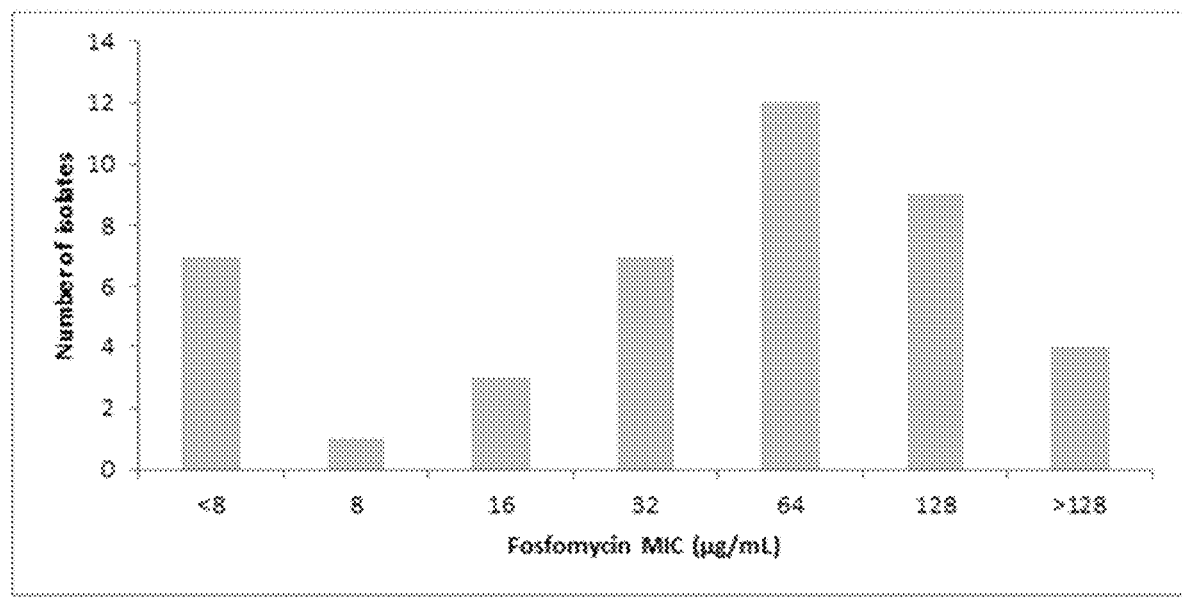
FIG. 2 shows a distribution of FOS MICs relative to certain isolates as tested.

Seventy percent of isolates were CR (NS to either MER or IMP). As single agents, CFT-TAZ (88% S), CAZ-AVI (74% S), FOS (70% S) and GEN (70% S) were most active. The distribution of FOS MICs is shown in FIG. 2. Synergy rates for FOS in combination with other agents, as determined by double disc diffusion, are presented in Table 5.

TABLE 5

Synergy between FOS and Other Agents, Based on Disc Diffusion

| Isolates tested | Combinations (% synergy (n)) | | | | | | |
|---|---|---|---|---|---|---|---|
|  | FOS + C/A | FOS + C/T | FOS + CIP | FOS + GEN | FOS + MER | FOS + IMP | FOS + P/T |
| All isolates | 42% (18/43) | 30% (13/43) | 35% (15/43) | 5% (2/43) | 7% (3/43) | 14% (6/43) | 7% (3/43) |
| FOS-S isolates | 60% (18/30) | 43% (13/30) | 40% (12/30) | 3% (1/30) | 10% (3/30) | 20% (6/30) | 10% (3/30) |
| FOS-R isolates | 0% (0/13) | 0% (0/13) | 23% (3/13) | 0% (0/13) | 0% (0/13) | 0% (0/13) | 0% (0/13) |

Synergy was most common for FOS+CAZ-AVI (42%), FOS+CIP (35%), and FOS+CFT-TAZ (30%). For FOS+CAZ-AVI and FOS+CFT-TAZ, synergy was observed exclusively against isolates that were FOS-S (synergy rates: 60% and 43%, respectively). For FOS+CIP, synergy was more likely against isolates that were FOS-S than FOS-R (40% vs. 23%). Tested alone in time-kills against FOS-S isolates, CAZ-AVI, CFT-TAZ and PIP-TAZ were bactericidal against 8% (1/12) of isolates. Rates of bactericidal activity and synergy for FOS combined with CAZ-AVI, CFT-TAZ and PIP-TAZ are presented in Table 6. Synergy rates were 67%, 83% and 50%, respectively, which was higher for each combination than observed by disc diffusion.

TABLE 6

Bactericidal Activity and Synergy for FOS Combined with Other Agents, Based on Time-Kills

| Outcome of interaction | Combinations (% (n)) | | |
|---|---|---|---|
|  | FOS + CAZ/AVI | FOS + CFT-TAZ | FOS + PIP-TAZ |
| Fungicidal activity | 50% (6/12) | 50% (6/12) | 17% (2/12) |
| Synergy | 67% (8/12) | 83% (10/12) | 50% (6/12) |

CONCLUSIONS

FOS was active against a collection of CR- and otherwise highly drug-resistant Pa isolates, with susceptibility rates comparable to the new β-lactam/β-lactamase inhibitors CFT-TAZ and CAZ-AVI. Moreover, FOS was synergistic with ceftolozane-tazobactam (CFT-TAZ) and ceftazidime-avibactam (CAZ-AVI) against a majority of FOS-S isolates, as measured by time-kills. FOS also demonstrated synergy with CIP (disc diffusion) and PIP-TAZ (time-kills) against 40% and 50% of isolates, respectively. Therefore, FOS is a promising agent against infections due to CR- and highly drug-resistant Pa, in particular as part of combination regimens with other active agents.

It will be appreciated that details of the foregoing embodiments, given for purposes of illustration, are not to be construed as limiting the scope of this invention. Although several embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all the advantages of some embodiments, particularly of the preferred embodiments, yet the absence of a particular advantage shall not be construed to necessarily mean that such an embodiment is outside the scope of the present invention.

What is claimed is:

1. A method of treating a Gram-negative bacterial infection, comprising a co-administration regimen of an effective amount of fosfomycin together with an effective amount of piperacillin-tazobactam, ceftolozane-tazobactam or ceftazidime-avibactam to an infected subject, wherein the bacterial infection is an infection with a carbapenem resistant mutant subpopulation of the Gram-negative bacteria.

2. The method of claim 1, wherein the Gram-negative bacterial infection is an infection caused by *Klebsiella pneumoniae*.

3. The method of claim 1, wherein the Gram-negative bacterial infection is an infection caused by *Pseudomonas aeruginosa*.

4. The method of claim 1, wherein the Gram-negative bacterial infection is an infection caused by *Acinetobacter baumannii*.

5. The method of claim 1, wherein the effective amount of fosfomycin is greater than the effective amount of the at least one antimicrobial agent when co-administered to the infected subject.

6. The method of claim 1, wherein the effective amount of fosfomycin is less than the effective amount of the at least one antimicrobial agent when co-administered to the infected subject.

7. A method of treating a subject with a bacterial infection that includes infection with a carbapenem resistant mutant subpopulation selected from the group consisting of *Staphylococcus aureus, Enterococcus faecalis, Pseudomonas aeruginosa, Acinetobacter baumannii* and *E. coli*, the method comprising:

a. obtaining a sample from a subject suffering from a bacterial infection;

b. identifying the presence of the carbapenem resistant mutant subpopulation in said sample; and c. co-administering fosfomycin and an effective amount of piperacillin-tazobactam, ceftolozane-tazobactam or ceftazidime-avibactam to the subject, wherein after the co-administration, the bacterial density is effectively reduced and the carbapenem resistant mutant subpopulation is inhibited.

8. The method of claim 7, wherein the effective amount of fosfomycin is greater than the effective amount of the at least one antimicrobial agent when co-administered to the infected subject.

9. The method of claim 7, wherein the effective amount of fosfomycin is less than the effective amount of the at least one antimicrobial agent when co-administered to the infected subject.

* * * * *